US007002056B2

(12) United States Patent
Gingera et al.

(10) Patent No.: US 7,002,056 B2
(45) Date of Patent: Feb. 21, 2006

(54) **HERBICIDE TOLERANT *BRASSICA JUNCEA* AND METHOD OF PRODUCTION**

(75) Inventors: Gregory R. Gingera, Saskatoon (CA); Jayantilal D. Patel, Thornhill (CA); David G. Charne, Guelph (CA); Rakesh K. Arora, Ghaziabad, U.P. (IN)

(73) Assignee: Pioneer Hi-Bred International, Inc., Johnston, IA (US)

( * ) Notice: Subject to any disclaimer, the term of this patent is extended or adjusted under 35 U.S.C. 154(b) by 345 days.

(21) Appl. No.: 10/096,172

(22) Filed: Mar. 12, 2002

(65) Prior Publication Data

US 2002/0138866 A1 Sep. 26, 2002

Related U.S. Application Data

(62) Division of application No. 09/522,798, filed on Mar. 10, 2000, now Pat. No. 6,613,963.

(51) Int. Cl.
*A01H 1/00* (2006.01)
*A01H 4/00* (2006.01)

(52) U.S. Cl. ...................................... 800/266; 435/418
(58) Field of Classification Search ................ 435/418, 435/419; 800/266, 298, 300, 306, 269
See application file for complete search history.

(56) References Cited

U.S. PATENT DOCUMENTS

| | | | |
|---|---|---|---|
| 5,387,758 A | 2/1995 | Wong et al. | 800/264 |
| 5,545,821 A | 8/1996 | Wong et al. | 800/300 |
| 5,767,366 A | 6/1998 | Sathasivan et al. | 800/300 |
| 5,773,702 A | 6/1998 | Penner et al. | 800/268 |
| 5,850,009 A * | 12/1998 | Kevern | 800/271 |
| 6,303,849 B1 | 10/2001 | Potts et al. | 800/306 |
| 6,613,963 B1 * | 9/2003 | Gingera et al. | 800/306 |

OTHER PUBLICATIONS

Hattori et al 1995 Molecular and General Genetics, 246: 419-425.*
Swanson et al 1989 Theoretical and Applied Genetics 78: 525-530.*
Miki, et al., 1990, *Theoretical and Applied Genetics*, 80: 449-458, "Transformation of *Brassica napus* canola cultivars with *Arabidopsis thaliana* acetohydroxyacid synthase genes and analysis of herbicide resistance".
Swanson, et al., 1988, *Plant Cell Reports*, 7:83-87, "The characterization of herbicide tolerant plants in *Brassica napus* L. after in vitro selection of microspores and protoplasts".
Rutledge, et al., 1991, *Mol. Gen. Genet.*, 229:31-40, "Molecular characterization and genetic origin of the *Brassica napus* acetohydroxyacid synthase multigene family".
Ouellet, et al., 1992, *Plant Journal*, 2:321-330, "Members of the acetohydroxyacid synthase multigene family of *Brassica napus* have divergent patterns of expression".

Hattori, et al., 1992, *Can J. Bot.*, 70: 1957-1963, "DNA sequence relationships and origins of acetohydroxy acid synthase genes of *Brassica napus*".
Swanson, et al., 1989, *Theor. Appl. Genet.*, 78:525-530, "Microspore mutagenesis and selection: Canola plants with field tolerance to imidazolinones".
Newhouse, et al., 1992, *Plant Physiol.*, 100:882-886, "Tolerance to imidazolinone herbicides in wheat".
Sprague, et al., 1997, *Weed Technology*, 11:241-247, "Common cocklebur (*Xanthium strumarium*) resistance to selected ALS-inhibiting herbicides".
Wright, et al., 1998, *Weed Science*, 46:24-29, "In vitro and whole-plant magnitude and cross-resistance characterization of two imidazolinone-resistant sugarbeet (*Beta vulgaris*) somatic cell selections".
Seefeldt, et al., 1998, *Weed Science*, 46:632-634, "Production of herbicide-resistant jointed goatgrass (*Aegilops cylindrica*) x wheat (*Triticum aestivum*) hybrids in the field by natural hybridization".
Harms, et al., 1992, *Mol. Gen. Genet.*, 233:427-435, "Herbicide resistance due to amplification of a mutant acetohydroxyacid synthase gene".
Lee, et al., 1988, *The Embro Journal*, 7:1241-1248, "The molecular basis of sulfonylurea herbicide resistance in tobacco".
Lovell, et al., 1996, *Weed Science*, 44:789-794, "Imidazolinone and sulfonylurea resistance in a biotype of common waterhemp (*Amaranthus rudis*)".
Foes, et al., 1999, *Weed Science*, 47:20-27, "A kochia (*Kochia scoparia*) biotype resistant to triazine and ALS-inhibiting herbicides".
Bing, D., 1991, M. Sc. Thesis, University of Saskatchewan, "Potential of gene transfer among oilseed brassica and their weedy relatives".
Newhouse, et al., 1988, *American Chemical Society Symposium Series Managing Resistance to Agrochemicals*, 421:474-482, "Genetic Modification of Crop Responses to Imidazolinone Herbicides".
Fehr, W.R. et al. "Mutation Breeding." 1987, Principles of Cultivar Development, vol. 1, pp 286-303.

(Continued)

*Primary Examiner*—David H Kruse
(74) *Attorney, Agent, or Firm*—Pioneer Hi-Bred International, Inc.

(57) ABSTRACT

The invention is in the field of *Brassica juncea* breeding (i.e., *Brassica* breeding), specifically relating to the development of stable herbicide tolerant *Brassica juncea* lines, plants and plant parts produced from a line designated 98SJ-238XX. A method of producing stable herbicide tolerant *Brassica juncea* lines, plants and plant parts from the *Brassica juncea* line designated 98SJ-238XX is also provided.

2 Claims, 3 Drawing Sheets

OTHER PUBLICATIONS

Hattori, J. et al. "An acetohydroxy acid synthase mutant reveals a single site involved in multiple herbicide resistance." 1995, Mol Gen Genet, vol. 246, pp 419-425.

Hobbs, S.L.A. "Comparison of Photosynthesis in Normal and Triazine-Resistant" 1987, Can. J. Plant Sci., vol. 67, pp. 457-466.

Bing et al., "Hybridizations among *Brassica napus, B. rapa* and *B. juncea* and their two weedy relatives *B. nigra* and *Sinapis arvensis* under open pollination conditions in the field", (1996), Plant Breeding, 115: 470-473.

* cited by examiner

Drawing 1: Genomic constitution of certain Brassica species (U, 1935).
Amphidiploids listed in bold text Brassica rapa
                Diploid
                Genome - AA

Brassica napus        Brassica juncea
Amphidiploid         Amphidiploid
Genome - AACC      Genome - AABB

Brassica oleraceae                      Brassica nigra
Diploid                                            Diploid
Genome - CC                        Genome - BB

Brassica carinata
                Amphidiploid
                Genome - BBCC

Drawing 2: Breeding procedure used to develop herbicide tolerant Brassica juncea

| Females | Male |
|---|---|
| Bulk population from<br>16 Brassica juncea breeding lines<br>low glucosinolate (9-18 umoles)<br>low erucic acid (<1%) | 46A72 |

Crossed to produce the F1

| Female | Males |
|---|---|
| F1 from previous cross<br>13 F1 lines x 15 plants per line<br>Selected with Pursuit® 50ml/ha a.i.<br>Chose resistant plants for crossing | Bulk pollen from 16 breeding lines –<br>F5 to F8 generation<br>low glucosinolate (<8 um)<br>low erucic acid (< 0.5%) |

Crossed to produce BC1

| Female | Males |
|---|---|
| BC1 populations from previous cross<br>6 BC1 populations x 36 plants per line<br>Selected with Pursuit® - 50 ml/ha a.i.<br>Chose resistant plants for crossing | Bulk pollen from16 breeding lines –<br>F5 to F8 generation<br>low glucosinolate (<8 umoles)<br>low erucic acid (<0.5%) |

Crossed to produce BC2

| Female | Males |
|---|---|
| BC2 seed from previous cross<br>4 BC populations<br>Selected with Pursuit® – 50 ml /ha a.i.<br>Chose resistant plants for crossing | Bulk pollen from 3 breeding lines –<br>F6 generation<br>low glucosinolate (6 to 12 umoles)<br>low erucic acid (<0.5%) |

Crossed to produce BC3

Stable juncea phenotype combined with Pursuit® tolerance
Lines coded:   98SJ-23841, 98SJ-23844, 98SJ-23845

Drawing 3: Greenhouse and field evaluation of Herbicide tolerant Brassica juncea populations

Greenhouse evaluation 1 – verify tolerance and juncea phenotype

98SJ-23841, 98SJ-23844, 98SJ-23845 and unstable BC3 sister lines planted for herbicide tolerance evaluation Pursuit® applied at 50 ml/ha a.i.; juncea phenotype stable Survivors self pollinated and harvested

---

Greenhouse evaluation 2 – verify tolerance and juncea phenotype

Survivors from previous project planted for herbicide tolerance evaluation

Pursuit® applied at 50 ml/ha a.i.; juncea phenotype and tolerance stable in 98SJ-23841, 98SJ-23844 and 98SJ-23845

Survivors self pollinated and harvested

---

Field evaluation 1 – verify tolerance and juncea phenotype under field conditions Pioneer Hi-Bred International Puerto Vallarta Mexico Research Station Self-pollinated selections from all other previous projects were planted at a single location Odyssey® was applied at 30g/ha a.i.

Juncea phenotype stable – tolerance present in 98SJ-23841, 98SJ-23844 and 98SJ-23845 progenies Other material derived from other generations and breeding lines exhibited a range of tolerance ranging from fully resistant, intermediate resistant and susceptible. Plant phenotypes ranged from full Brassica napus to Brassica juncea phenotypes and lines and populations that exhibited traits that were intermediate between Brassica napus and Brassica juncea. In these other materials, full resistance to the herbicide was not associated with the juncea phenotype, and vice-versa.

HERBICIDE TOLERANT *BRASSICA JUNCEA* AND METHOD OF PRODUCTION

CROSS-REFERENCE TO RELATED APPLICATIONS

This application is a divisional of U.S. application Ser. No. 09/522,798 filed Mar. 10, 2000, now U.S. Pat. No. 6,613,963, which is herein incorporated by reference.

FIELD OF THE INVENTION

The invention is in the field of *Brassica juncea* breeding (i.e., *Brassica*), specifically relating to the development of stable herbicide tolerant *Brassica juncea* lines, plants and plant parts. A method of producing stable herbicide tolerant *Brassica juncea* lines, plants and plant parts is also provided.

BACKGROUND OF THE INVENTION

Several *Brassica* species are recognized as an increasingly important oilseed crop and a source of high quality protein meal in many parts of the world. The oil extracted from the seeds commonly contains a lesser concentration of endogenously formed saturated fatty acids than other vegetable oils and is well suited for use in the production of salad oil or other food products or in cooking or frying applications. The oil also finds utility in industrial applications. Additionally, the meal component of the seeds can be used as a nutritious protein concentrate for livestock.

The three primary *Brassica* species currently utilized for *Brassica* production and development are *Brassica napus*, *Brassica rapa* and *Brassica juncea*, each of which belong to the family Brassicaceae. *Brassica juncea* is currently grown as an oilseed in India and China. As *Brassica juncea* tolerates heat and drought conditions to a greater extent than *Brassica napus* and *Brassica rapa*, there is potential for *Brassica juncea* production in certain areas of the United States, Canada and Australia. Table 1 contains a comparative description of the general characteristics of *Brassica napus*, *Brassica rapa* and *Brassica juncea* compiling information from the Canola Council of Canada worldwide web site and the USDA circular number C857 by Albina Musil USDA1950C857 (1951).

*Brassica juncea* is commonly grown as a condiment mustard species in several countries including Canada, Hungary, Poland, Ukraine, China, Nepal and India. Mustard quality *Brassica juncea* is typically high in glucosinolate and high in erucic acid content, but is relatively low in oil content. Mustard seed can be used in whole seed or crushed form. Seed may be milled into flour or the oil may be extracted for use in cooking. High glucosinolate and high erucic acid types are quality variants within the same species, differing only in quality parameters. As a result, cross breeding between low and high glucosinolate or erucic acid genotypes are easily made.

Certain genotypes of *Brassica juncea* generally possess relatively low erucic acid levels in the oil and low glucosinolate levels in the meal. Therefore, certain commercial varieties of *Brassica juncea* may be developed that can be termed "CANOLA®" in accordance with the trademark of the Canola Council of Canada, which refers to forms of oilseed *Brassica* with erucic acid of <2% in the oil and total glucosinolates of <30 micromoles/gram of defatted meal.

TABLE 1

Key morphological differences separating *Brassica napus*, *Brassica juncea* and *Brassica rapa* oilseeds and mustards

| Trait/Species | *Brassica napus* | *Brassica juncea* | *Brassica rapa* |
|---|---|---|---|
| Growth habit | Spring and Winter | Spring | Spring and Winter |
| Cotyledon morphology | Smooth on underside<br>Large - 5/8 to 7/8 inches across<br>Heart-shaped cotyledon and dark green in color | Small - 5/16 to 9/16 inch across<br>Less lobed than *napus* - lighter green color | Spiny and wrinkled on underside<br>Small - 5/16 to 9/16 inch across<br>Less lobed than *napus* - lighter green color |
| First leaf morphology | Oblong or shield shaped, thin, bluish-green in color, smooth with a few hairs near the margin | Oblong, bright green and hairy | Oblong, bright green to light bluish-green, sparingly hairy |
| Flowers | Buds borne above open flowers | Open flowers borne above buds | Compact bud clusters, buds held below uppermost open flowers |
| Pollination | Principally self-pollinating and mostly self-compatible | Principally self-pollinating and mostly self-compatible | Principally cross-pollinated and self-incompatible (although there is one self-pollinating, self-compatible variety known as Yellow sarson) |
| Leaf morphology | Leaf blade only partially clasps stem<br>Lyrate in form | Small petiole attaches leaf to stem<br>Margins with irregular shallow indentations | Leaf blade clasps stem completely<br>Roughly oblong with coarsely toothed margins |
| Seed color | Black | Brown and/or yellow | Brown and/or yellow |
| Ploidy | Amphidiploid (AACC)<br>2 copies of *rapa* genome (AA)<br>2 copies of *oleraceae* genome (CC) | Amphidiploid (AABB)<br>2 copies of *rapa* genome (AA)<br>2 copies of *nigra* genome (BB) | Diploid (AA)<br>2 copies of *rapa* genome (AA) |

The genomic composition of canola species are as follows (FIG. 1). *Brassica rapa*, a diploid species, contains only the A (*rapa*) genome and has a genomic constitution of AA. *Brassica napus* is an amphidiploid with the *rapa* (A) and *oleraceae* (C) genomes and is listed as AACC. *Brassica juncea* is also an amphidiploid with the rapa (A) genome and the nigra (B) genome. Genetically, *Brassica juncea* is listed as AABB.

During pollen and ovule formation, the chromosomes within each genome will pair with their homologues (i.e., 'A' chromosomes will pair with 'A', 'B' will pair with 'B'), and it is extremely rare to have pairing of A and B or A and C. This pairing may be forced by repeated crossing and careful selection of plant phenotype during breeding, although there is no expectation that a trait from one genome may be combined with a trait from the other genome.

*Brassica* sp. cultivars are developed through breeding programs that utilize techniques such as mass and recurrent selection, backcrossing, pedigree breeding and haploidy. Recurrent selection is used to improve populations of either self or cross-pollinating *Brassica*. Through recurrent selection, a genetically variable population of heterozygous individuals is created by intercrossing several different parents. The best plants are selected based on individual superiority, outstanding progeny, or excellent combining ability. The selected plants are intercrossed to produce a new population in which further cycles of selection are continued. Various recurrent selection techniques are used to improve quantitatively inherited traits controlled by numerous genes.

Breeding programs use backcross breeding to transfer genes for a simply inherited, highly heritable trait into another line that serves as the recurrent parent. The source of the trait to be transferred is called the donor parent. After the initial cross, individual plants possessing the desired trait of the donor parent are selected and are crossed (backcrossed) to the recurrent parent for several generations. The resulting plant is expected to have the attributes of the recurrent parent and the desirable trait transferred from the donor parent. This approach has been used for breeding disease resistant phenotypes of many plant species. However, certain traits are difficult to transfer by backcross breeding because other attributes of the recurrent parent are linked to the desirable trait, and therefore it is difficult to develop a resulting plant with all of the attributes of the recurrent parent and the desirable trait transferred from the donor parent. Backcrossing has been used to transfer low erucic acid and low glucosinolate content into lines and breeding populations of *Brassica*.

Pedigree breeding and recurrent selection breeding methods are used to develop lines from breeding populations. Pedigree breeding starts with the crossing of two genotypes, each of which may have one or more desirable characteristics that is lacking in the other or which complements the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1$ to $F_2$; $F_2$ to $F_3$; $F_3$ to $F_4$; $F_4$ to $F_5$, etc. For example, two parents that are believed to possess favorable complementary traits are crossed to produce an $F_1$. An $F_2$ population is produced by selfing one or several $F_1$'s or by intercrossing two $F_1$'s (i.e., sib mating). Selection of the best individuals may begin in the $F_2$ population, and beginning in the $F_3$ the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines commonly are tested for potential release as new cultivars. Backcrossing may be used in conjunction with pedigree breeding; for example, a combination of backcrossing and pedigree breeding with recurrent selection has been used to incorporate blackleg resistance into certain cultivars of *Brassica napus*.

Plants that have been self-pollinated and selected for type for many generations become homozygous at almost all gene loci and produce a uniform population of true breeding progeny. If desired, the haploidy method can also be used to extract homogeneous lines. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

The choice of breeding or selection methods depends on the mode of plant reproduction, the heritability of the trait(s) being improved, and the type of cultivar used commercially (e.g., $F_1$ hybrid cultivar, pureline cultivar, etc.).

SUMMARY OF THE INVENTION

The invention is in the field of *Brassica juncea* (i.e. *Brassica*) breeding, specifically relating to the development of stable herbicide tolerant *Brassica juncea* lines, plants and plant parts. A method of producing stable herbicide tolerant *Brassica juncea* lines, plants and plant parts is also provided.

BRIEF DESCRIPTION OF THE DRAWINGS

FIG. 1: Genomic constitution of certain *Brassica* species (U, 1935). Amphidiploids listed in bold text FIG. 2: Breeding procedure used to develop herbicide tolerant *Brassica juncea*

FIG. 3: Greenhouse and field evaluation of Herbicide tolerant *Brassica Juncea* populations

DEFINITIONS

In the description and tables which follow a number of terms are used. In order to aid in a clear and consistent understanding of the specification the following definitions and evaluation criteria are provided.

Cotyledon. A cotyledon is a type of seed leaf that is contained on a plant embryo. A cotyledon contains the food storage tissues of the seed. The embryo is a small plant contained within a mature seed.

Cotyledon Length. The distance between the indentation at the top of the cotyledon and the point where the width of the petiole is approximately 4 mm.

Cotyledon Width. The width at the widest point of the cotyledon when the plant is at the two to three-leaf stage of development (mean of 50).

Fatty Acid Content: The typical percentages by weight of fatty acids present in the endogenously formed oil of the mature whole dried seeds are determined. During such determination, the seeds are crushed and are extracted as fatty acid methyl esters following reaction with methanol and sodium methoxide. Next the resulting ester is analyzed for fatty acid content by gas liquid chromatography using a capillary column which allows separation on the basis of the degree of unsaturation and fatty acid chain length. This procedure is described in the work of J. K. Daun et al. *J. Amer. Oil Chem. Soc.,* 60: 1751 to 1754 (1983) which is herein incorporated by reference.

Flower Bud Location. A determination is made whether typical buds are disposed above or below the most recently opened flowers.

Glucosinolate Content. The total aliphatic glucosinolate content of the meal of the seeds is determined on the moisture free air-dried-oil-free solid meal as measured by the gas liquid chromatography method of the Canadian Grain Commission as is expressed micromoles per gram. Capillary gas chromatography of the trimethylsityl derivatives of extracted and purified desulfoglucosinolates with optimization to obtain optimum indole glucosinolate detection as described in *"Procedures of the Western Canada Canola/Rapeseed Recommending Committee Incorporated for the Evaluation and Recommendation for Registration of Canola/Rapeseed Candidate Cultivars in Western Canada"*.

Growth Habit. This refers to whether the *Brassica* is primarily a spring annual or winter annual type.

Herbicide Tolerance. Tolerance to various herbicides when applied at standard recommended application rates is expressed on a scale of 1 (highly tolerant), 2 (tolerant), or 3 (susceptible).

Leaf Morphology. Includes characteristics such as leaf attachment to stem, leaf color, leaf dentation, leaf margin hairiness. Often observed on first leaves and again when at least 6 leaves of the plant are completely developed.

Mutagenesis. Any one of many techniques known in the art to create or induce genetic mutations, including, without limitation, microspore mutagenesis as described in Swanson et al., *Plant Cell Reports* 7:83–87 (1989).

Oil Content. The typical percentage by weight oil present in the mature whole dried seeds is determined by ISO 10565:1993 Oilseeds Simultaneous determination of oil and water—Pulsed NMR method.

Plant Height. The overall plant height at the end of flowering is observed (mean of 50).

Ploidy. This refers to whether the number of "basic sets" of chromosomes (individual replicates of the same genome) exhibited by the cultivar is diploid (two sets) or amphidiploid (two sets each of two different genomes).

Resistance to Shattering. Resistance to silique shattering is observed at seed maturity and is expressed on a scale of 1 (poor) to 5 (excellent).

Seed Coat Color. The seed coat color of typical mature seeds is observed.

DETAILED DESCRIPTION OF THE INVENTION

A *Brassica* breeding population should be substantially homogenous and reproducible to be useful in either further breeding or the development of a commercial cultivar. There are a number of analytical methods available to determine the phenotypic stability of a *Brassica* population.

The oldest and most traditional method of analysis is the observation of phenotypic traits. The data is usually collected in field experiments over the life of the *Brassica* plants to be examined. Phenotypic characteristics most often are observed for traits associated with seed yield, seed oil content, seed protein content, fatty acid composition of oil, glucosinolate content of meal, growth habit, lodging resistance, plant height, shattering resistance, etc. Other phenotypic characteristics commonly observed include resistance to disease, insects and tolerance to herbicides. Herbicide tolerance is particularly important for *Brassica*, since many weeds, such as stinkweed, shepherd's purse, flixweed, ball mustard, wormseed mustard, hare's ear mustard and common peppergrass have a close genetic relationship with *Brassica*. Therefore, it is advantageous for a cultivar to have herbicide tolerance not possessed by related weeds or even undesired *Brassica* plants of a different variety or cultivar.

Herbicides may function by disrupting amino acid biosynthesis in affected species. For example, the imidazolinone herbicides are active on the enzyme acetohydroxy acid synthase (AHAS), the first enzyme in the biosynthesis of the amino acids leucine, isoleucine and valine. Imidazolinone herbicide tolerance prevents inhibition of the AHAS enzyme, allowing tolerant plants to continue with normal amino acid biosynthesis.

Most forms of *Brassica napus, Brassica rapa* and *Brassica juncea* are highly susceptible to herbicides, such as imidazolinones. Doses of imidazolinone herbicides applied during our backcross breeding program were sufficient to kill susceptible *Brassica juncea* and *Brassica napus* checks as well as material segregating away from herbicide tolerance.

Swanson et al., *Plant Cell Reports* 7:83–87 (1989) reported the development of imidazolinone herbicide tolerant *Brassica napus* mutants using microspore mutagenesis. During the process, five fertile double-haploid *Brassica napus* plants were developed. One of the mutants was tolerant to between 5 and 10 times recommended field rates of an imidazolinone herbicide. An inheritance study indicated that two semi-dominant unlinked genes combined to develop an F1 with greater tolerance than either of the parents. The mutants were subsequently crossed with other breeding material to develop Pioneer variety 46A72.

Rutledge et al. *Mol. Gen. Genet.* 229:31–40 (1991) proposed a model for the inheritance of the AHAS genes in *Brassica napus*. AHAS2, AHAS3 and AHAS4 appear to be linked with the A (*rapa*) genome and AHAS1 and AHAS5 are likely associated with the C (*oleraceae*) genome. AHAS1 and AHAS3 were expressed at all growth stages (Ouellet et al., *Plant J.* 2:321–330 1992) and mutant forms of AHAS1 and AHAS3 appear to be the most effective tolerance genes. AHAS2 was found to be active only in ovules and seeds. AHAS4 was found to be defective due to interrupted sequences in the middle of the coding region (Rutledge et al., *Mol. Gen. Genet* 229:31–40, 1991) and was not expressed in tissues examined by Ouellet et al. *Plant J.* 2:321–330, (1992). The last gene, AHAS5, may also be defective (Rutledge et al. *Mol. Gen. Genet* 229:31–40, 1991). Hattori et al. *Can J. Bot:* 70: 1957–1963, (1992) determined that the DNA sequence of coding regions for AHAS1 and AHAS3 were 98% identical. DNA sequences of the 5' and 3' ends were also closely related. Few genetic similarities were observed between the sequences of AHAS2 as compared to AHAS1 or AHAS3 genes.

Thus, there are only two known effective genes for imidazolinone herbicide tolerance—an AHAS1 mutant (believed to be located on the C genome) and an AHAS3 mutant (believed to be located on the A genome). As *Brassica juncea, Brassica napus* and *Brassica rapa* all contain the A genome (FIG. 1), transfer of the AHAS3 mutant gene is a simple matter of crossing the species and selecting under herbicide selection as normal genome recombinations would likely allow for the complete transfer of the mutant AHAS3 coding segments. A single AHAS tolerance gene will provide some protection under very low screening rates of herbicides. Under high screening rates (such as were used in the greenhouse and field screening protocols), genotypes possessing the single AHAS1 tolerance gene do not die, but are severely stunted, grow multiple racemes and are very late to flower and mature. In our normal screening program, we discarded these individuals. Accordingly, both AHAS1 and AHAS3 mutant genes appear to be required for the levels of tolerance evaluated in these experiments.

Because mutant forms of both genes appear to be required for full tolerance, the mutant AHAS3 gene and the mutant AHAS1 gene (believed to be on the C genome) must be transferred into the same genotype. *Brassica juncea* and *Brassica rapa* do not contain the C genome, which is one reason why there have been no commercial herbicide tolerant *Brassica juncea* and *Brassica rapa* varieties developed to date. Herbicide tolerance provided by only a single mutant AHAS gene is insufficient to protect otherwise susceptible plants from field application rates of herbicides. Attempts up until this research to transfer the mutant AHAS1 gene and the corresponding herbicide tolerance trait to *Brassica rapa* and *Brassica juncea* have proven to be very difficult.

In the present invention, herbicide tolerant *Brassica juncea* was developed through a backcross breeding program. 46A72, a Pioneer Hi-Bred herbicide tolerant *Brassica napus* commercial variety, was used as the trait donor. The herbicide tolerance trait in 46A72 was developed through mutagenic techniques described by Swanson, et al. (1989). PHI research has confirmed that there is some level of cross-tolerance between the tolerance sources for imidazolinone herbicides and sulfonyl urea herbicides. 46A72 (the donor parent) has been shown to be tolerant to sulfonyl urea herbicides as well as imidazolinone herbicides. 46A72 is available from Pioneer Hi-Bred International, Inc., 400 Locust Street, Des Moines, Iowa 50309.

The first step in the development of the herbicide tolerant *Brassica juncea* lines was to cross the herbicide tolerant *Brassica napus* variety 46A72 with low glucosinolate and low erucic acid *Brassica juncea* lines (FIG. 2) using the *Brassica juncea* parents as females. The seeds and plants resulting from this cross are referred to as the F1 generation. The F1 generation was used as a female to receive pollen from *Brassica juncea* lines to develop the BC1 generation. The BC1 was used as a female parent to receive pollen from *Brassica juncea* lines to produce the BC2. A third round of crossing was used to produce the BC3. The F1, BC1 and BC2 generations were screened for herbicide tolerance by using Pursuit® herbicide at a rate of 50 ml/ha (1×field rate), or Odyssey® herbicide at a rate of 30 g/ha (1×field rate). Both herbicides are available from American Home Products, Inc., American Cyanamid Division, 5 Giralda Farms, Madison, N.J., 07940, and Pursuit® and Odyssey® are trademarks owned by American Home Products, Inc. Plants exhibiting satisfactory levels of herbicide tolerance during the herbicide tolerance program were crossed and selected. The screening, crossing and selection was repeated, and the first stable herbicide tolerant *Brassica juncea* phenotypes (designated 98SJ-23841, 98SJ-23844 and 98SJ-23845) were produced at the BC3 generation. Each of lines 98SJ-23841, 98SJ-23844 and 98SJ-23845are substantially stable and reproducible for both herbicide tolerance and the *Brassica juncea* phenotype.

There were other related BC3 materials (unstable sister populations of 98SJ-23841, 98SJ-23844 and 98SJ-23845) that varied for herbicide tolerance and plant phenotype. These BC3 materials exhibited less stability for the *Brassica juncea* phenotype as they ranged from plants with a complete *Brassica napus* phenotype to plants with a complete *Brassica juncea* phenotype. There were also a large number of plants in the sister populations that exhibited various combinations of plant traits from either *Brassica napus* or *Brassica juncea*. These unstable sister populations continued to segregate for plant phenotype traits with continued selfing and evaluation. The unstable sister populations also segregated for herbicide tolerance as plants ranged between complete tolerance, intermediate tolerance and full susceptibility to the herbicide. During the evaluation of fully tolerant materials prior to the BC3 generation, we found no evidence of complete tolerance associated with a complete *Brassica juncea* phenotype. Many of the intermediate tolerance plants had *Brassica juncea* characteristics, but had insufficient levels of tolerance to protect the plants from herbicide damage during screening and evaluation.

The second step in developing the herbicide tolerance was to verify stability in subsequent generations (FIG. 3).

Unexpected difficulties were encountered in the backcross breeding program as a result of the linkage between the *Brassica napus* phenotype and the herbicide tolerant trait. During the first three rounds of crossing (F1, BC1 and BC2) all of the plants which inherited the herbicide tolerance trait also inherited the *Brassica napus* phenotype, or their selfed progeny reverted back to the *Brassica napus* phenotype in subsequent generations. Conversely, plants that did not inherit the herbicide tolerance trait inherited the *Brassica juncea* phenotype. Thus, it was only through great effort involving many crosses and careful selection within BC2 segregating materials that the three populations (98SJ-23841, 98SJ-23844 and 98SJ-23845) were developed that expressed both the *Brassica juncea* phenotype and the herbicide tolerance trait. Presumably, the necessary genetic change that allowed for the simultaneous expression of a fully fertile *Brassica juncea* plant phenotype in combination with herbicide tolerance occurred between the BC2 and BC3.

98SJ-23841, 98SJ-23844 and 98SJ-23845 were the first populations to show uniformity and stability for the *juncea* phenotype and herbicide tolerance. Each of these three populations demonstrated a substantial degree of herbicide tolerance. Successive selfed progenies derived from these three backcross populations have also exhibited stable herbicide tolerance and continue to maintain the *Brassica juncea* phenotype under greenhouse and field evaluation. In addition, it is known to those skilled in the art that herbicide tolerance genes in *Brassica napus* commonly confer cross-tolerance to sulfonyl urea herbicides.

As can be seen in Table 2, the stable herbicide resistant lines 98SJ-23841, 98SJ-23844 and 98SJ-23845 are phenotypically similar to *Brassica juncea* line 96SJ-3827 used in their development. They are also phenotypically different from *Brassica napus* trait donor 46A72, with the exception that they possess the herbicide tolerance trait of 46A72.

TABLE 2

Phenotypic descriptions of 46A72 (*Brassica napus* donor), a *juncea* breeding line used in the backcross procedure (96SJ-3827) and three breeding populations (98SJ-23841, 98SJ-23844 and 98SJ-23845) developed during the breeding process.

| Trait | *Brassica napus* trait donor 46A72 | 98SJ-23841 | 98SJ-23844 | 98SJ-23845 | 96SJ-3827 - *Brassica juncea* parent in BC1 and BC2 stage |
|---|---|---|---|---|---|
| Growth habit | Spring | Spring | Spring | Spring | Spring |

TABLE 2-continued

Phenotypic descriptions of 46A72 (*Brassica napus* donor), a *juncea* breeding line used in the backcross procedure (96SJ-3827) and three breeding populations (98SJ-23841, 98SJ-23844 and 98SJ-23845) developed during the breeding process.

| Trait | *Brassica napus* trait donor 46A72 | 98SJ-23841 | 98SJ-23844 | 98SJ-23845 | 96SJ-3827 - *Brassica juncea* parent in BC1 and BC2 stage |
|---|---|---|---|---|---|
| Cotyledon morphology | Large - 5/8 to 7/8 inches across Heart-shaped cotyledon and dark green in color | Small - 5/16 to 9/16 inch across Light green color | Small - 5/16 to 9/16 inch across Light green color | Small - 5/16 to 9/16 inch across Light green color | Small - 5/16 to 9/16 inch across Light green color |
| First leaf morphology | Bluish-green in color, smooth with a few hairs near the margin | Bright green and hairy | Bright green and hairy | Bright green and hairy | Bright green and hairy |
| Flowers | Buds borne above open flowers | Buds borne below open flowers | Buds borne below open flowers | Buds borne below open flowers | Buds borne below open flowers |
| Pollination | Self-pollinating and self-fertile | Self-pollinating and self-fertile | Self-pollinating and self-fertile | Self-pollinating and self-fertile | Self-pollinating and self-fertile |
| Leaf morphology | Leaf blade only partially clasps stem Blue-green in color | Small petiole attaches leaf to stem Bright green color | Small petiole attaches leaf to stem Bright green color | Small petiole attaches leaf to stem Bright green color | Small petiole attaches leaf to stem Bright green color |
| Pods | Larger and fewer pods Medium length beak | Small pods - 14–16 seeds per pod Long beak and flattened pods | Small pods - 14–16 seeds per pod Long beak and flattened pods | Small pods - 14–16 seeds per pod Long beak and flattened pods | Small pods - 14–16 seeds per pod Long beak and flattened pods |
| Resistance to shattering | Easily shattered when ripe | Resistant to shattering under greenhouse conditions | Resistant to shattering under greenhouse conditions | Resistant to shattering under greenhouse conditions | Resistant to shattering under field and greenhouse conditions |
| Seed color | Black | Yellow | Yellow Brown | Brown Yellow | Yellow |

Morphological

The herbicide tolerant *Brassica juncea* populations are each substantially resistant to herbicides and can be reproduced by planting seeds of such lines, growing the resulting *Brassica* plants under self-pollinating or sib-pollinating conditions with adequate isolation, and harvesting the resulting seed using conventional agronomic practices.

Development of Cultivars

The stable herbicide tolerant *Brassica juncea* populations can be used to develop new herbicide tolerant *Brassica juncea* cultivars by any manner known to those skilled in the art, such as crossing with other *Brassica juncea* lines, followed by selfing and selection of plants with the desired characteristics. The stable herbicide tolerant *Brassica juncea* lines may also be used as either donor lines or recurrent parents as part of a breeding program. Exposure to herbicide can be used to determine inheritance of the herbicide tolerance trait. Similarly, where a marker exists for a known gene or gene product, the breeder may use the marker to assist in determining which germplasm has inherited the trait and is suitable for advancement to the next generation.

Transformation of *Brassica*

With the advent of recombinant DNA techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign, additional and/or modified genes are referred to herein collectively as "transgenes", and plants containing one or more transgenes inserted into the plant genome through the use of recombinant DNA techniques are referred to as "transgenic plants." Over the last 15 to 20 years, several methods for producing transgenic plants have been developed, and the present invention, in particular embodiments, also relates to transformed versions of the claimed plant or line and to transformed versions of cultivars developed from such plant or line.

Plant transformation involves the construction of an expression vector, which will function in plant cells. Such a vector comprises a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed *Brassica* plants, using transformation methods known in the art to incorporate transgenes into the genetic material of the *Brassica* plant(s). Genes included in expression vectors must be driven by a nucleotide sequence comprising a regulatory element, for example, a promoter. Several types of promoters are now well known in the transformation arts, as are other regulatory elements that can be used alone or in combination with promoters. The term "promoter" includes reference to a region of DNA upstream from the start of transcription and involved in recognition and binding of RNA polymerase and other proteins to initiate transcription. Examples of promoters include promoters that preferentially initiate transcription in certain tissues, such as leaves, roots, seeds, fibers, xylem vessels, tracheids, or sclerenchyma. A "constitutive" promoter is a promoter which is active under most environmental conditions and in most tissue. With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below.

1. Genes That Confer Resistance to Pests or Disease and that Encode
    (a) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance to engineer plants that are resistant to specific pathogen strains.
    (b) A gene conferring resistance to fungal pathogens, such a oxalate oxidase or oxalate decarboxylase.
    (c) A *Bacillus thuringiensis* protein, a derivative thereof or a synthetic polypeptide modeled thereon.
    (d) A lectin.
    (e) A vitamin-binding protein such as avidin.
    (f) An enzyme inhibitor, for example, a protease or proteinase inhibitor or an amylase inhibitor.
    (g) An insect-specific hormone or pheromone such as an ecdysteroid and juvenile hormone, a variant thereof, a mimetic based thereon, or an antagonist or agonist thereof.
    (h) An insect-specific peptide or neuropeptide which, upon expression, disrupts the physiology of the affected pest.
    (i) An insect-specific venom produced in nature by a snake, a wasp, etc.
    (j) An enzyme responsible for an hyperaccumulation of a monterpene, a sesquiterpene, a steroid, hydroxamic acid, a phenylpropanoid derivative or another non-protein molecule with insecticidal activity.
    (k) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic.
    (l) A molecule that stimulates signal transduction.
    (m) A hydrophobic moment peptide.
    (n) A membrane permease, a channel former or a channel blocker.
    (o) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa, mosaic virus, cucumber mosaic virus, tobacco streak virus, potato virus X, potato virus Y, tobacco etch virus, tobacco rattle virus and tobacco mosaic virus.
    (p) An insect-specific antibody or an immunotoxin derived therefrom. Thus, an antibody targeted to a critical metabolic function in the insect gut would inactivate an affected enzyme, killing the insect.
    (q) A virus-specific antibody.
    (r) A developmental-arrestive protein produced in nature by a pathogen or a parasite. Thus, funal endo-1,4-D-polygalacturonases facilitate fungal colonization and plant nutrient release by solubilizing plant cell wall homo-α-1,4-D-galacturonase.
    (s) A developmental-arrestive protein produced in nature by a plant. For example, transgenic plants expressing the barley ribosome-inactivating gene have an increased resistance to fungal disease.
    (t) Genes involved in the Systemic Acquired Resistance (SAR) Response and/or the pathogenesis related genes.
    (u) Antifungal genes.

2. Genes that Confer Tolerance To A Herbicide
    (a) A herbicide that inhibits the growing point or meristem, such as an imidazolinone or a sulfonyl urea. Exemplary genes in this category code for mutant ALS and AHAS enzyme as described, for example, by Lee et al., EMBO J. 7: 1241 (1988), and Miki et al., Theor. Appl. Genet. 80: 449 (1990), respectively. Lines 98SJ-23841, 98SJ-23844 and 98SJ-23845 are not transgenic, although copies of mutant ALS or AHAS genes could be added to these lines by transgenic methods to further enhance their herbicide tolerance.
    (b) Glyphosate (resistance imparted by mutant 5-enolpyruvl-3-phosphikimate synthase (EPSP) and aroA genes, respectively) and other phosphono compounds such as glufosinate (phosphinothricin acetyl transferase, PAT) and *Streptomyces hygroscopicus* phosphinothricin-acetyl transferase, bar, genes), and pyridinoxy or phenoxy propionic acids and cycloshexones (ACCase inhibitor-encoding genes). See, for example, U.S. Pat. No. 4,940,835 to Shah et al., which discloses the nucleotide sequence of a form of EPSP which can confer glyphosate resistance. A DNA molecule encoding a mutant aroA gene can be obtained under ATCC accession No. 39256, and the nucleotide sequence of the mutant gene is disclosed in U.S. Pat. No. 4,769,061 to Comai. European patent application No. 0 333 033 to Kumada et al. and U.S. Pat. No. 4,975,374 to Goodman et al. disclose nucleotide sequences of glutamine synthetase genes which confer tolerance to herbicides such as L-phosphinothricin. The nucleotide sequence of a phosphinothricin-acetyltransferase gene is provided in European application No. 0 242 246 to Leemans et al. De Greef et al., *Bio/Technology* 7: 61 (1989), describe the production of transgenic plants that express chimeric bar genes coding for phosphinothricin acetyl transferase activity. Exemplary of genes conferring tolerance to phenoxy propionic acids and cycloshexones, such as sethoxydim and haloxyfop, are the Acc1-S1, Accl-S2 and Accl-S3 genes described by Marshall et al., *Theor. Appl. Genet.* 83: 435 (1992).

(c) A herbicide that inhibits photosynthesis, such as a triazine (psbA and gs+genes) and a benzonitrile (nitrilase gene). Przibilla et al., *Plant Cell* 3: 169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., *Biochem. J.* 285: 173 (1992).

3. Genes that Confer or Contribute To a Grain Trait (a) Modified fatty acid metabolism, for example, by transforming a plant with an antisense gene or stearoyl-ACP desaturase to increase stearic acid content of the plant.

(b) Decreased phytate content.

(c) Introduction of a phytase-encoding gene would enhance breakdown of phytate, adding more free phosphate to the transformed plant.

(d) A gene could be introduced that reduces phytate content. In maize, this, for example, could be accomplished by cloning and then reintroducing DNA associated with the single allele which is responsible for maize mutants characterized by low levels of phytic acid.

(e) Modified carbohydrate composition effected, for example, by transforming plants with a gene coding for an enzyme that alters the branching pattern of starch.

(f) Reduced green seed, by down regulation of the CAB gene in *Brassica* seed.

In addition to the categories noted above, genes that control pollination or self-compatibility may also be expressed in transformed plants.

Numerous methods for plant transformation have been developed, including biological and physical, plant transformation protocols. In addition, expression vectors and in vitro culture methods for plant cell or tissue transformation and regeneration of plants are available. These include, but are not limited to Agrobacterium-mediated transformation and direct gene transfer such as microprojectile bombardment or sonication. A transgenic variety produced by these methods could then be crossed, with another (non-transformed or transformed) variety, in order to produce a new transgenic variety. Alternatively, a genetic trait which has been engineered into a particular *Brassica* line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context. It is also known in the art to culture *Brassica* cells or protoplasts, and to regenerate plants therefrom.

This invention also is directed to methods for producing a *Brassica* plant by crossing a first parent *Brassica* plant with a second parent *Brassica* plant wherein the first or second parent *Brassica* plant is one of the stable herbicide tolerant lines. Further, both first and second parent *Brassica* plants can be the same or different line. Thus, any such methods using the lines as a parent are within the scope of the present invention. Advantageously, the lines of the present invention can be used in crosses with other, different, *Brassica* inbreds to produce first generation ($F_1$) *Brassica* hybrid seeds and plants with superior characteristics.

As used herein, the term "plant" includes plant cells, plant protoplasts, plant cell tissue cultures from which *Brassica* plants can be regenerated, such as plant calli, plant clumps, and plant cells that are intact in plants or parts of plants, including embryos, pollen, ovules, flowers, pods, leaves, roots, root tips, anthers, stalks, and the like.

INDUSTRIAL APPLICABILITY

The seed of 98SJ-23841, 98SJ-23844, and 98SJ-23845, the plant produced from such seed, a hybrid *Brassica* plant produced from the crossing of any of these lines, the resulting hybrid seed, and various parts of the hybrid *Brassica* plant can be utilized in the production of an edible vegetable oil or other food products in accordance with known techniques. The remaining solid meal component derived from seeds can be used as a nutritious livestock feed. *Brassica* populations 98SJ-23841, 98SJ-23844 and 98SJ-23845 can also be used as breeding lines to develop herbicide tolerant *Brassica* (including canola and mustard quality) cultivars.

Deposits

A deposit of the seed of 98SJ-23841, 98SJ-23844 and 98SJ-23845 is and has been maintained by Pioneer Hi-Bred International, Inc., 800 Capital Square, 400 Locust Street, Des Moines, Iowa 50309-2340, since prior to the filing date of this application. Access to this deposit will be available during the pendency of the application to the Commissioner of Patents and Trademarks and persons determined by the Commissioner to be entitled thereto upon request. Upon the maturation of this application into a patent, Applicant(s) will make available to the public without restriction a deposit of at least 2,500 seeds of each of 98SJ-23841, 98SJ-23844 and 98SJ-23845 deposited at the American Type Culture Collection (ATCC), Manassas, Va. 20852. The seeds deposited with the ATCC will be taken from the same deposit maintained at Pioneer Hi-Bred International, Inc. and described above. Additionally, Applicant(s) will comply with all of the requirements of 37 C.F.R. §§1.801–1.809, including providing an indication of the viability of the sample when the deposit is made. This deposit of the 98SJ-23841, 98SJ-23844 and 98SJ-23845 populations will be maintained in the ATCC, which is a public depository recognized by the Budapest Treaty, for a period of 30 years, or 5 years after the most recent request, or for the enforceable life of the patent, whichever is longer, and will be replaced if it ever becomes nonviable during that period. More specifically, seeds of populations 98SJ-23841, 98SJ-23844 and 98SJ-23845 were deposited under the terms of the Budapest Treaty at the ATCC where they have been assigned ATCC Accession Nos. PTA-1406, PTA-1407 and PTA-1408 respectively. Applicant(s) will impose no restrictions on the availability of the deposited material from the ATCC; however, Applicants have no authority to waive any restrictions imposed by law on the transfer of biological material or its transportation in commerce. Applicants do not waive any infringement of its rights granted under any patents or breeder's rights granted in any country including rights in the United States under this patent and/or under the Plant Variety Protection Act (7 USC 2321 et seq.).

The foregoing invention has been described in detail by way of illustration and example for purposes of exemplification. However, it will be apparent that changes and modifications such as single gene modifications and mutations, somaclonal variants, variant individuals selected from populations of the plants of the instant lines, and the like, are considered to be within the scope of the present invention.

What is claimed is:

1. A tissue culture of an herbicide tolerant *Brassica juncea* plant of the line designated 98SJ-238XX, wherein 98SJ-238XX is a member selected from the group consisting oft 98SJ-23841, representative seed of the line 988J-23841 having been deposited under ATCC Accession No. PTA-1406; 98SJ-23844, representative seed of the line 98SJ-23844 having been deposited under ATCC Accession No. PTA-1407; and 98SJ-23845, representative seed of the line 98SJ-23845 having been deposited under ATCC Accession No. PTA-1408.

2. A method for producing an herbicide tolerant *Brassica* plant, comprising:
   (a) crossing a *Brassica* 98SJ-238XX plant with a second *Brassica juncea* plant to yield progeny *Brassica* seed, and
   (b) growing said progeny *Brassica* seed and selecting for imidazolinone tolerant progeny plants; wherein 98J-238XX is a member selected from the group consisting of 98SJ-23841, representative seed of the line 98SJ-23841 having been deposited under ATCC Accession No. PTA-1406, 98SJ-23844, representative seed of the line 98SJ-23844 having been deposited under ATCC Accession No. PTA-1407, and 98SJ-23845, representative seed of the line 98SJ-23845 having been deposited under ATCC Accession No. PTA-1408.

* * * * *

UNITED STATES PATENT AND TRADEMARK OFFICE
CERTIFICATE OF CORRECTION

PATENT NO. : 7,002,056 B2 Page 1 of 1
APPLICATION NO. : 10/096172
DATED : February 21, 2006
INVENTOR(S) : Gregory R. Gingera et al.

It is certified that error appears in the above-identified patent and that said Letters Patent is hereby corrected as shown below:

<u>Column 15, line 16 - Column 16, line 4,</u>
Should read:
-- A tissue culture of an herbicide tolerant *Brassica juncea* plant of the line designated 98SJ-238XX, wherein 98SJ-238XX is a member selected from the group consisting of: 98SJ-23841, representative seed of the line 98SJ-23841 having been deposited under ATCC Accession No. PTA-1406, 98SJ-23844, representative seed of the line 98SJ-23844 having been deposited under ATCC Accession No. PTA-1407; and 98SJ-23845, representative seed of the line 98SJ-23845 having been deposited under ATCC Accession No. PTA-1408. --.

<u>Column 16,</u>
Lines 5-19, should read:
-- A method for producing an herbicide tolerant *Brassica* plant, comprising:
    (a) crossing a *Brassica* 98SJ-238XX plant with a second *Brassica juncea* plant to yield progeny *Brassica* seed, and
    (b) growing said progeny *Brassica* seed and selecting for imidazolinone tolerant progeny plants; wherein 98SJ-238XX is a member selected from the group consisting of, 98SJ-23841, representative seed of the line 98SJ-23841 having been deposited under ATCC Accession No. PTA-1406, 98SJ-23844, representative seed of the line 98SJ-23844 having been deposited under ATCC Accession No. PTA-107, and 98SJ-23845, representative seed of the line 98SJ-23845 having been deposited under ATCC Accession No. PTA-1408. --.

Signed and Sealed this

Twenty-seventh Day of June, 2006

JON W. DUDAS
*Director of the United States Patent and Trademark Office*